United States Patent [19]

Richardson

[11] 4,230,099
[45] Oct. 28, 1980

[54] DEVICE FOR ALINING THE SPINE

[76] Inventor: Billy H. Richardson, 9140 Millbranch, Southaven, Miss. 38671

[21] Appl. No.: 13,629

[22] Filed: Feb. 21, 1979

[51] Int. Cl.³ .............................................. A61F 5/00
[52] U.S. Cl. .................................................... 128/69
[58] Field of Search ...................... 128/69, 78, 68, 82, 128/83

[56] References Cited

U.S. PATENT DOCUMENTS

| | | | |
|---|---|---|---|
| 712,375 | 10/1902 | Hartford | 128/69 |
| 726,055 | 4/1903 | Hartford | 128/69 |
| 1,134,181 | 4/1915 | Bump | 128/69 |
| 1,572,794 | 2/1926 | Hamilton | 128/69 |
| 1,617,593 | 2/1927 | Hardy | 128/69 |
| 1,833,426 | 11/1931 | Knudson | 128/69 |

Primary Examiner—John D. Yasko

[57] ABSTRACT

A device for being positioned beneath the back of a human lying supine on a support surface to aline that human's spine. Two upwardly extending elongated ridge members are joined together in a substantially parallel and alined position. Each ridge member has a first end and a second end and an upper surface. The upper surface of each ridge member forms a convex curve substantially at the first end thereof that substantially corresponds to the natural lumbar curve of a human spine, forms a concave curve intermediate the first and second ends thereof that substantially corresponds to the natural thoracic curve of a human spine, and forms a convex curve substantially at the second end thereof that is slightly less than the normal cervical curve of a human spine.

11 Claims, 10 Drawing Figures

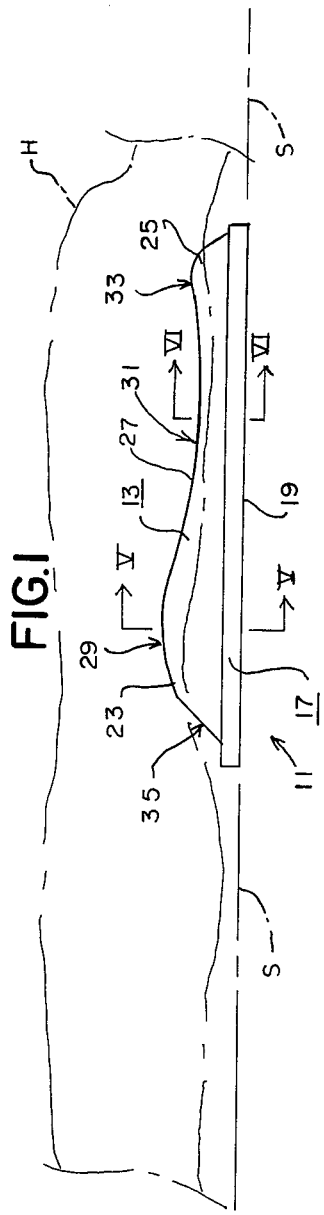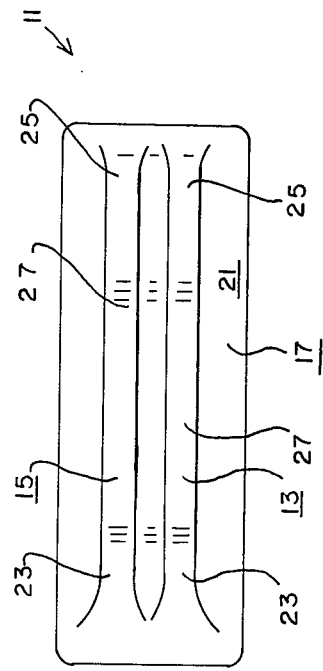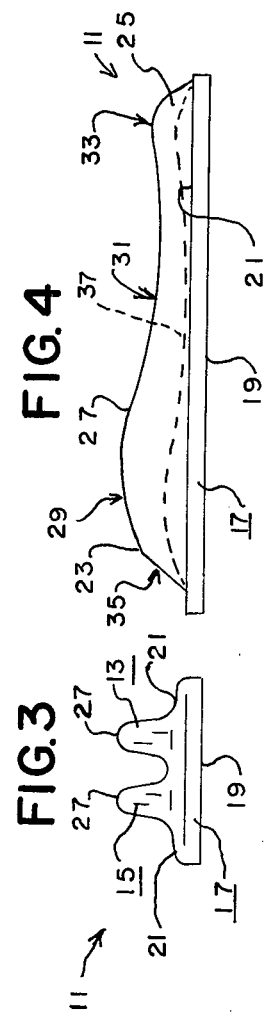

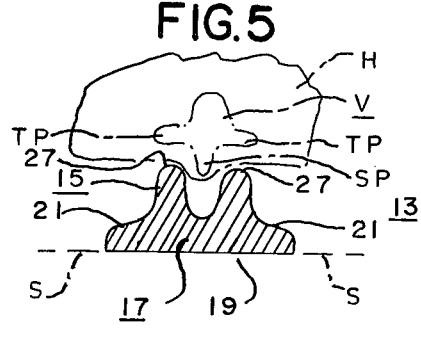
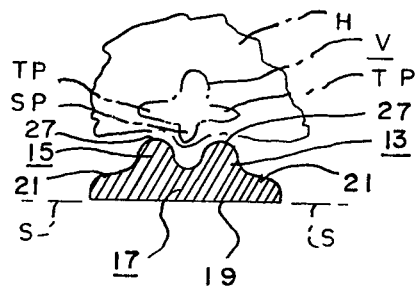
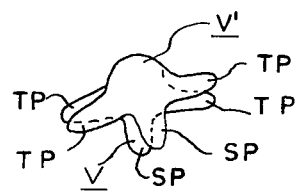
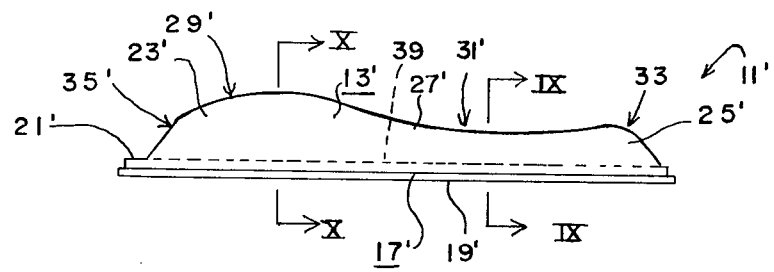
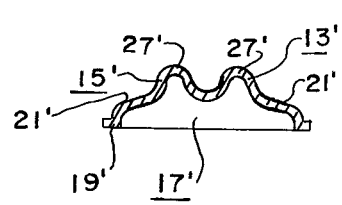
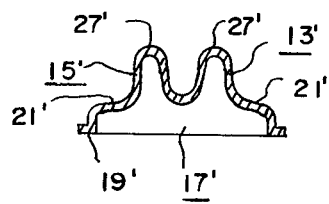

DEVICE FOR ALINING THE SPINE

BACKGROUND OF THE INVENTION

1. Field of the Invention

The present invention relates generally to devices and aids for relieving back pains, reducing tension of the back, alleviating stress and strain of the back and applies acupressure to backs, shoulders and legs.

2. Description of the Prior Art

Heretofore, various devices and aids have been developed to relieve back pain and the like. For example, many types of back braces, belts, etc., are presently or have been previously available. However, back pain and the like is often a result of a misalined vertebra of the spine which results in pinched nerves and the like. Such misalinement in the past has required medical care such as the application of traction and/or chiropractic manipulation.

SUMMARY OF THE PRESENT INVENTION

The present invention is directed towards providing a device for use in alining the spine which does not require the application or traction and/or chiropractic manipulation. The concept of the present invention is to provide a device in which first and second elongated ridge members are held substantially parallel to and alined with one another at a substantially constant distance apart and to shape the upper surface of each ridge member so as to form a convex curve substantially at one end thereof and a concave curve intermediate the opposite ends thereof. The convex curve perferably substantially corresponds to the natural lumbar curve of a human spine. The concave curve preferably substantially corresponds to the natural thoracic curve of a human spine. The ridge members are preferably spaced apart from one another a distance more than the normal thickness of the spinous processes of a human spine and less than the normal width of the vertebra of a human spine. When a person lies supine with his spine substantially alined between the ridge members, any misalinement of his vertebra will be corrected.

BRIEF DESCRIPTION OF THE DRAWINGS

FIG. 1 is a side elevational view of the device of the present invention shown in use.

FIG. 2 is a top plan view of the device of the present invention.

FIG. 3 is an end elevational view thereof.

FIG. 4 is a side elevational view thereof similar of FIG. 1 but with the device shown alone.

FIG. 5 is a sectional view as taken on line V—V of FIG. 1.

FIG. 6 is a sectional view as taken on line VI—VI of FIG. 1.

FIG. 7 is a somewhat diagrammatic end view of a pair of vertebrae of a human spine with one of the vertebrae misalined.

FIG. 8 is a side elevational view of an alternate embodiment of the device of the present invention.

FIG. 9 is a sectional view as taken on line IX—IX of FIG. 8.

FIG. 10 is a sectional view as taken on line X—X of FIG. 8.

DESCRIPTION OF THE PREFERRED EMBODIMENT

The device 11 of the present invention is for use in alining a human spine. More specifically, the device 11 is for being positioned beneath the back of a human H lying supine on a supporting surface S such as a floor or the like to aline that human's spine. The need for alining the spine occurs when one or more vertebra V of the spine becomes misalined with one another. For example, a vertebra V' may twist axially out of alinement with the other vertebrae V of the spine as diagrammatically depicted in FIG. 7. When such misalinement occurs, back pain and/or nervous tension of the back and/or stress and strain of the back will occur. The device 11 is intended to correct such problems without the necessity of applying traction and/or chiropractic manipulation, etc.

The device 11 includes, in general, a first elongated ridge member 13 and a second elongated ridge member 15 held substantially parallel to and alined with one another at a substantially constant distance apart from one another by a bridge means. Preferably, the device 11 includes a base member 17 having a bottom surface 19 for resting on the support surface S and having a top surface 21 to which the ridge members 13, 15 are fixedly attached and which acts as the bridge means.

Each ridge member 13, 15 has a first end 23, a second end 25, and an upper surface 27. Preferably, the ridge members 13, 15 and the base member 17 are constructed as a one-piece integral unit. For example, the ridge members 13, 15 and base member 17 can be molded or cast out of plastic as a unitary part.

The upper surface 27 of each ridge member 13, 15 forms a convex curve as at 29 substantially at the first end 23 thereof and forms a concave curve as at 31 intermediate the first and second ends 23, 25 thereof. Preferably, the upper surface 27 of each ridge member 13, 15 also forms a convex curve as at 33 substantially at the second end 25 thereof. The convex curve 29 preferably substantially corresponds to the natural lumbar curve of a human spine. The concave curve 31 preferably substantially corresponds to the natural thoracic curve of a human spine. The convex curve 33 is preferably slightly less than the normal cervical curve of a human spine. The first and second ridge members 13, 15 are preferably located apart from one another a distance more than the normal thickness of the spinous processes SP of a human spine and less than the normal width of the vertebra of a human spine as diagrammatically indicated in FIGS. 5 and 6. The upper surface 27 of the ridge members 13, 15 preferably forms a substantially flat, sloping area as at 35 adjacent the first end 23 thereof. All edges and corners of the top surface 21 of the base member 17 and the first and second ridge members 13, 15 are preferably rounded so as to alleviate the possibility of any sharp edges cutting into the user of the device 11.

The operation and use of the device 11 is quite simple. The device 11 is placed on a supporting surface S that is large enough for a human H to lie supine on such as a floor or the like. The human H then lies on the supporting surface S with his spine substantially alined between the ridge members 13, 15 as diagrammatically indicated by FIGS. 1, 5 and 6 and with the flat area 35 of each member 13, 15 positioned substantially adjacent his ilium, with the convex curve 29 of each ridge member 13, 15 positioned substantially adjacent the lumbar curve of his spine, and with the concave curve 31 of each ridge member 13, 15 positioned substantially adjacent the thoracic curve of his spine. The ridge members 13, 15 will then extend on either side of the spinous processes SP of the human's spine whereby pressure will be applied against the transverse processes TP of the human's spine and whereby any misalined vertebra thereof will be alined. It should be noted that more pressure will be applied to certain areas of the spine if the human H changes his positioned with respect to the device 11. More specifically by simply raising his arms, the human H will cause more pressure to be applied to the thoracic curve region of his spine. By simply raising his knees, the human H will cause more pressure to be applied to the lumbar curve region of his spine.

The present invention may be constructed as a solid as clearly shown in FIGS. 5 and 6. On the other hand, FIGS. 8, 9 and 10 show an alternate embodiment of the present invention in which the present invention is constructed in a hollow manner. More specifically, FIGS. 8, 9 and 10 discloses a device 11' substantially similar to the device 11 heretofore disclosed having a first elongated ridge member 13', a second elongated ridge member 15', a base member 17' having a bottom surface 19' and a top surface 21', and with each of the ridge members 13', 15' having a first end 23', a second end 25' and an upper surface 27'. The upper surface 27' of each ridge member 13', 15' forms a convex curve 29' substantially at the first end 23' thereof, a concave curve 31' intermediate the first and second end 23', 25' thereof, a convex curve 33' substantially at the second end 25' thereof, and a flat, sloping area 35' at the first end 23' thereof with substantially the same relationship to a human spine as the upper surface 27 of the ridge members 13, 15 of the device 11.

The present invention may be constructed out of various materials and in various manners as will be apparent to those skilled in the art. For example, the present invention may be molded of fiberglass or plaster or plastic. It may be constructed in various sizes for the specific person that plans to utilize it. However, as long as the above mentioned limitations are maintained, one size of the present invention will accomodate most humans. The portion of the top surface 21 base member 17 between the first and second ridge members 13, 15 may be substantially parallel to the upper surface 27 of the first and second ridge members 13, 15 as indicated by the broken line referred to by the numeral 37 in FIG. 4, or may be substantially parallel to the bottom surface 19 of the base means 17 or the supporting surface S as indicated by the broken line referred to by the numeral 39 in FIG. 8.

Although, the present invention has been described and illustrated with respect to preferred embodiment thereof, it is not to be so limited since changes and modifications may be made therein which are within the full intended scope of the invention.

I claim:

1. A device for use in alining a human spine, said device comprising: first and second elongated ridge members and a bridge means for holding said first and second elongated ridge members substantially parallel to and alined with one another at a substantially constant distance apart from one another, each of said ridge members having a first end and a second end and an upper surface, said upper surface of each of said ridge members being continuous and gently curved and forming a convex curve substantially at said first end thereof, forming a concave curve intermediate said first and second ends thereof and forming a substantially flat, sloping area adjacent said first end thereof.

2. The device of claim 1 in which said upper surface of each of said ridge members forms a convex curve substantially at said second end thereof.

3. The device of claim 2 in which said convex curve formed by said upper surface of each of said ridge members substantially at said first end thereof substantially corresponds to the natural lumbar curve of a human spine.

4. The device of claim 3 in which said concave curve formed by said upper surface of each of said ridge members intermediate said first and second ends thereof substantially corresponds to the natural thoracic curve of a human spine.

5. The device of claim 4 in which said convex curve formed by said upper surface of each of said ridge members substantially at said second end thereof is slightly less than the normal cervical curve of a human spine.

6. The device of claims 1 or 5 in which said first and second ridge members are held apart from one another a distance more than the normal thickness of the spinous processes of a human spine and less than the normal width of the vertebrae of a human spine.

7. A device for being positioned beneath the back of a human lying suprine on a supporting surface to aline that human's spine, said device comprising:
(a) a base member for resting on said support surface;
(b) a first upwardly extending elongated ridge member positioned on said base member, said first ridge member having a first end and a second end and having an upper surface, said upper surface of said first ridge member forming a convex curve substantially at said first end thereof, forming a concave curve intermediate said first and second ends thereof, and forming a substantially flat, sloping area adjacent said first end thereof; and
(c) a second upwardly extending elongated ridge member positioned on said base member substantially parallel to and alined with said first ridge member and spaced apart from said first ridge member at a substantially constant distance, said second ridge member having a first end and a second end and having an upper surface, said upper surface of said second ridge member being continuous and gently curved and forming a convex curve substantially at said first end thereof, forming a concave curve intermediate said first and second ends thereof, and forming a substantially flat, sloping area adjacent said first end thereof.

8. The device of claim 7 in which said convex curve formed by said upper surfaces of each of said ridge members substantially at said first ends thereof substantially corresponds to the natural lumbar curve of said human's spine.

9. The device of claim 8 in which said concave curve formed by said upper surfaces of each of said ridge members intermediate said first and second ends thereof substantially corresponds to the natural thoracic curve of said human's spine.

10. The device of claim 9 in which said upper surface of each of said ridge members form a convex curve substantially at said second end thereof, said convex curve formed by said upper surfaces of each of said ridge members substantially at said second ends thereof being slightly less than the normal cervical curve of said human's spine.

11. The device of claims 7 or 10 in which said first and second ridge members are positioned apart from one another a distance more than the normal thickness of a spinous process of said human's spine and less than the normal width of a vertebra of said human's spine.

* * * * *